(12) United States Patent
Marciano et al.

(10) Patent No.: US 10,957,421 B2
(45) Date of Patent: Mar. 23, 2021

(54) SYSTEM AND METHOD FOR INTER-SPECIES DNA MIXTURE INTERPRETATION

(71) Applicants: Michael Marciano, Manlius, NY (US); Jonathan Adelman, Mexico, NY (US)

(72) Inventors: Michael Marciano, Manlius, NY (US); Jonathan Adelman, Mexico, NY (US)

(73) Assignee: Syracuse University, Syracuse, NY (US)

(*) Notice: Subject to any disclaimer, the term of this patent is extended or adjusted under 35 U.S.C. 154(b) by 0 days.

(21) Appl. No.: 14/957,873

(22) Filed: Dec. 3, 2015

(65) Prior Publication Data

US 2016/0162636 A1 Jun. 9, 2016

Related U.S. Application Data

(60) Provisional application No. 62/086,874, filed on Dec. 3, 2014.

(51) Int. Cl.
*G16B 40/00* (2019.01)
*G16B 30/00* (2019.01)

(52) U.S. Cl.
CPC .............. *G16B 40/00* (2019.02); *G16B 30/00* (2019.02)

(58) Field of Classification Search
CPC .......... G06F 19/22; G06F 19/18; G06F 19/24; G06F 17/30598; G06F 17/30867; G06F 19/20; G06F 19/28; G06F 19/3431; G06F 19/3443; G06F 17/00; G06F 17/27; G06F 17/30112; G06F 19/10; G06F 19/12; G06F 19/322; G06F 17/30; G06F 17/30321; G06F 17/30424; G06F 17/30442; G06F 17/30657; G06F 17/3071; G06F 19/14; G06F 19/26; G06F 17/30327; G06F 17/30333; G06F 17/30554; G06F 19/00; G06F 16/00; G06F 16/248; G06F 16/9024; G06F 17/18; G06F 16/2246; G06F 16/2264; G06F 16/285; G06F 17/246; G06F 16/22; G06F 17/153; G06F 16/215; C12Q 2537/165; C12Q 1/6888; C12Q 1/6806; C12Q 1/6869; C12Q 2535/122; C12Q 2537/143; C12Q 2600/156; C12Q 1/6827; C12Q 1/686; C12Q 1/6874; C12Q 1/682; C12Q 1/6844; C12Q 1/68; C12Q 1/6809; C12Q 1/6846; C12Q 2537/16; C12Q 1/6851; C12Q 1/6858; C12Q 2531/113; C12Q 2545/114; C12Q 2565/627; C12Q 1/6837; C12Q 2527/137; C12Q 2535/125; C12Q 2545/10; C12Q 1/00; G06K 9/00288; G06K 9/6256; G06K 9/627; G06K 9/481; G06K 9/0014; G06K 9/00281; G06K 9/6215; G06K 9/628; G06K 9/4628; G06K 9/6267; G06K 9/6262; G06K 9/6269; G06K 9/00147; G06K 2209/07; G06K 9/6201; G06K 9/6218; G06K 9/6234; G06K 9/6265; G06K 9/6276; G06K 9/66; G06N 99/005; G06N 5/043; G06N 3/08; G06N 33/57488; G06N 3/02; G06N 7/005; G06N 20/00; G06N 3/0427; G06N 3/088; G06N 5/022; G06N 5/04; G06N 20/10; G06N 3/0454; G06N 20/20; G06N 3/04; G06N 5/003; G06N 2800/60; G01N 33/57488; G01N 1/02; G01N 2001/002; G01N 21/6486; G01N 21/94; G01N 27/4145; G01N 27/4148; G01N 2800/60; G05B 13/028; G05B 2219/32287; G05B 2219/35001; G05B 23/0221; G05B 23/0229; G05B 23/024; G05B 23/0294; G05B 2219/40115; G05B 19/042; G05B 2219/23253; G05B 2219/25255; G05B 2219/25268; G05B 2219/33333; G16B 20/00; G16B 30/00;

(Continued)

(56) References Cited

U.S. PATENT DOCUMENTS 6,214,556 B1 4/2001 Olek et al.
6,741,983 B1 5/2004 Birdwell et al.
(Continued)

FOREIGN PATENT DOCUMENTS

WO 1999066302 12/1999

OTHER PUBLICATIONS

Cowell, R. G. et al. Identification and separation of DNA mixtures using peak area information, Forensic Science International, vol. 166 pp. 28-34, 2007.*

(Continued)

*Primary Examiner* — Mary K Zeman
(74) *Attorney, Agent, or Firm* — Bond Schoeneck and King PLLC; David Nocilly

(57) ABSTRACT

Methods and systems for characterizing two or more nucleic acids in a sample. The method can include the steps of providing a hybrid machine learning approach that enables rapid and automated deconvolution of DNA mixtures of multiple contributors. The input is analyzed by an expert system which is implemented in the form of a rule set. The rule set establishes requirements based on expectations on the biology and methods used. The methods and systems also include a machine learning algorithm that is either incorporated into the expert system, or utilizes the output of the expert system for analysis. The machine learning algorithm can be any of a variety of different algorithms or combinations of algorithms used to perform classification in a complex data environment.

6 Claims, 4 Drawing Sheets

(58) Field of Classification Search
CPC .......... G16B 40/00; G16B 50/00; G16B 5/00;
G16B 35/00; G16B 15/00; G16B 45/00;
G16B 99/00; G16B 25/00; G16B 20/10;
G16B 40/20; G16B 10/00; G16B 20/20;
G16B 25/20; G16B 40/30; G16B 25/10;
G16B 40/10; G16B 30/10; G16B 5/20;
G16B 50/30; C12N 15/1065; C12N
15/11; C12N 15/1065; C12N 15/1089;
G16H 50/20; G16H 40/63; G16H 10/60;
G16H 50/80; G16H 10/40; G16H 15/00;
G16H 50/70; G16H 70/20; C40B 40/06;
C40B 20/06; C40B 60/10; G06Q 50/24;
G06Q 50/22; G06T 11/206; G06T
2207/20041; G06T 2207/30072; G06T
7/97; G06T 7/0014; G06T 2207/20081;
G06T 2207/20084; B01L 3/50; Y02A
90/24; Y10S 707/99932; Y10S
707/99933; Y10S 707/99935; Y10S
707/99942; Y10S 707/99945; G16C
20/70
USPC ..................................................... 702/19–28
See application file for complete search history.

(56) References Cited

U.S. PATENT DOCUMENTS

| | | | |
|---|---|---|---|
| 7,272,506 B2 | 9/2007 | Glanowski et al. | |
| 7,624,087 B2* | 11/2009 | Birdwell ................. | G06N 5/04 706/60 |
| 7,664,719 B2 | 2/2010 | Birdwell et al. | |
| 7,840,358 B2 | 11/2010 | Jojic | |
| 7,968,350 B2 | 6/2011 | Chait | |
| 8,898,021 B2* | 11/2014 | Perlin ................. | C12Q 1/6851 702/19 |
| 2005/0042639 A1 | 2/2005 | Knapp et al. | |
| 2005/0136480 A1 | 6/2005 | Brahmachari et al. | |
| 2009/0006002 A1* | 1/2009 | Honisch ............... | C12Q 1/6858 702/20 |
| 2009/0148835 A1* | 6/2009 | Cave ...................... | G16B 20/00 435/6.1 |
| 2009/0170712 A1 | 7/2009 | Beatty et al. | |
| 2009/0270264 A1* | 10/2009 | Overson ................. | C40B 20/06 506/5 |
| 2012/0283955 A1 | 8/2012 | Cameron et al. | |
| 2014/0052383 A1* | 2/2014 | Larson .................. | G16B 30/00 702/20 |
| 2016/0232282 A1* | 8/2016 | Overson ................. | C40B 20/06 |

OTHER PUBLICATIONS

Murdoch, M C et al. 1991 A multilayer perceptron feature extractor for reading sequenced DNA autoradiograms. Neural Networks for Signal Processing Proceedings of the 1991 IEEE Workshop. pp. 562-569.*

Taylor et al. The interpretation of single source and mixed DNA profiles. 2013 Forensic Science International: genetics vol. 7 p. 516-528.*

Stoffel, K. Fuzzy clustering based methodology for multidimensional data analysis in computational forensic domain. (2012) Int J of Comp Info Sys and Industrial Management Apps, vol. 4 p. 400-410.*

Scherbina Short tandem repeat (STR) profile authentication via Machine learning techniques. (2012) MS degree, MIT 171 pages.*

Bille, et al. Comparison of the performance of different models for the interpretation of low-level mixed DNA profiles. (2014) Electrophoresis, vol. 35 p. 1325-3133.*

Lee, C. et al., May 2010, "Inferring Ethnicity From Mitochondrial DNA Sequence", BioMed Central Ltd., 6th International Symposium on Bioinformatics Research and Applications (ISBRA'10, BMC Proceedings, Article 5, Supplemental 2:S11, pp. 1-9.

Pourmand, N. et al., Apr. 10, 2007, "Branch Migration Displacement Assay with Automated Heuristic Analysis for Discrete DNA Length Measurement Using DNA Microarrays", PNAS, vol. 104, No. 15, pp. 6146-6151.

Rafeh, R. and Mesgar, M., 2009, "Neural Network in Human Identification by DNA Sequences", IEEE Computer Society, Second International Conference on Computer and Electrical Engineering, DOI 10.1109/ICCEE.2009.132, pp. 64-67.

Stoffel, K. et al., "Fuzzy Methods for Forensic Data Analysis", Institute of Forensic Science, University of Lausanne, pp. 1-6.

* cited by examiner

| Software output | Analyst | Computational | Validation data |
|---|---|---|---|
| Total DNA amplified | Inhibitors present | Peak height / sequence count balance/intensity balance/ratios | Peak/intensity amplitude threshold |
| Injection time (CE only)/ Volume added to reaction | Stochastic/low levels | Intra locus/count height/intensity ratios | Match interpretation (stochastic) threshold |
| Inter-run baseline | Intra-run baseline | | Heterozygote balance |
| Intra-run baseline | Injection quality | "small"/ large locus ratios | Artifact morphologies |
| Allele (s)- sequence or basepair size | Inter-run baseline | Allelic dropout/in | Stutter %-locus |
| Data point (CE- only) | Data point (CE- only) | Minimum, Maximum, Estimated # contributors | Stutter %-inter locus |
| Peak height/ sequence count | Peak height | Locus specific count/peak amplitude threshold | Instrument sensitivity (LOD) |
| Peak width | Peak morphology | | Primer PCR efficiency |
| Peak Area | Degradation present | Allele specific stutter and heterozygote balance | |
| Sequence Quality Metrics (ex-Phred) | Artifacts- pull-up, spikes, sequence errors | Weighted pre- MLA deconvoluted genotypes | |
| Sequence variants | Relevant sequences/ peaks | Degradation | |

FIG. 4

SYSTEM AND METHOD FOR INTER-SPECIES DNA MIXTURE INTERPRETATION

CROSS-REFERENCE TO RELATED APPLICATIONS

This application claims priority to U.S. Provisional Patent Application Ser. No. 62/086,874, filed on Dec. 3, 2014 and entitled "System and Method for Inter-Species DNA Mixture Interpretation," the entire disclosure of which is incorporated herein by reference.

BACKGROUND

The present invention relates to methods for identifying nucleic acid in a sample and, more particularly, to methods and systems for performing DNA mixture interpretation using a hybrid machine learning approach.

At the core of the genetic identification field, particularly in regard to forensic applications and clinical/medical research, is the challenge of DNA mixture interpretation. A DNA sample mixture can be defined as a mixture of two or more biological samples, and mastery of their interpretation can greatly impact the course of criminal investigations and/or quality of intelligence. The two primary components of mixture analysis are at least: (1) the identification of the minimum number of contributors to the sample, followed by (2) an attempt at mixture deconvolution.

Although historically expert systems have been in use for this problem, they often fail to meet the needs of the community, and there is continued demand by forensic communities for reliable methods of automation for mixture interpretation. The present state-of-the-art in DNA mixture interpretation includes expert systems which often have limited use, primarily focusing on improving the timeliness of analysis performed by forensic analysts. These systems capture the computational aspects of mixture analysis without taking more subjective factors into account. Further, these systems are used for simple mixtures, typically of two individuals (and thus low complexity). Although more advanced systems capable of analyzing 3-4 individual mixtures exists, these systems are both time- and cost-prohibitive.

Accordingly, there is a need in the art for methods and systems that perform complicated DNA mixture interpretation in both a time-effective and cost-effective manner.

BRIEF SUMMARY

The present disclosure is directed to methods and systems for performing DNA mixture interpretation using a hybrid machine learning approach in both a time-effective and cost-effective manner. Further, the methods and systems allow access to information that may previously have been considered too laborious to collect and utilize efficiently and logically, including but not limited to environmental factors, characterizations and/or comparisons of DNA mixtures based on groups of contributors, and more capable deconvolution of mixtures of three or more individuals in a more efficient manner. In addition, various embodiments consider more subjective facets of a DNA profile and the related deposition and/or collection event, thereby providing significant information/intelligence as to the individuals (including across species) that have deposited biological on specific samples.

Accordingly, embodiments of the invention are directed to an automated, intelligent system capable of performing cutting-edge DNA mixture interpretation using a hybrid machine learning approach. System parameters can be drawn from among four groups of data: software output, analyst (human) input, computational input, and validation data, among others. The software output data set can be obtained through the use of a software program that can adequately provide metrics for those parameters which are critical to the analysis. Critical elements of this data set will be the quantitative assessment of the DNA types present at each DNA locus. The analyst input can encompass various data that cannot be captured in the laboratory analysis of the DNA sample or expert systems currently available do not have the capacity to determine, and can include the presence of low level data, DNA degradation, environmental conditions during the deposition/collection/transport of the sample, location of collection, and/or other known intelligence regarding sample collection. The computationally intensive data set can be an automated method of extracting relevant data from the raw data set. The validation data can be a laboratory dependent static data set that will be included in every analysis. This data set can provide foundational metrics which the downstream analyses of unknown samples will be based. These data will include metrics for the instrumentation and chemistries used to obtain DNA profiles. These parameters can then be input directly into a hybrid neural network, for example.

In one aspect is a method for characterizing two or more nucleic acids in a sample, comprising the steps of: (i) providing a machine learning mixture deconvolution system; (ii) characterizing a parameter (s) of the two or more nucleic acids; (iii) providing said characterized parameter to said machine learning mixture deconvolution system; and (iv) determining a source of at least one of said two or more nucleic acids.

According to an embodiment, the characterizing step comprises the step of performing fragment analysis or sequencing one or more bases of the two or more nucleic acids.

According to an embodiment, the method includes the step of obtaining the sample.

According to an embodiment, the two or more nucleic acids comprise at least one nucleic acid from two or more organisms, and/or from two or more species.

According to an embodiment, the determining step comprises identifying a species comprising at least one of the two or more nucleic acids, and/or identifying an individual comprising at least one of the two or more nucleic acids.

According to an aspect, a computer system configured to characterize two or more nucleic acids in a sample is provided. The computer system includes a machine learning module configured to receive a parameter of the two or more nucleic acids, and further configured to receive input from one or more of the following input modules: (i) a software input/output module configured to provide input comprising a metric for the parameter of the two or more nucleic acids; (ii) an analyst input module configured to provide input comprising information about the sample; (iii) a computational input module configured to provide input comprising instructions for extracting data from the machine learning module; and (iv) a validation data module configured to provide input comprising information about a standard data set; where the machine learning module is further configured to process the input from the one or more input modules to determine a source and/or identity of at least one of the two or more nucleic acids.

According to an embodiment, the machine learning module comprises a layer of neurons comprising a plurality of IF-THEN rules.

According to an embodiment, the parameter is selected from the group consisting of: total DNA amplified, sequence-SNP and length variants, a phred score, an inter-run baseline, an intra-run baseline, an allele or basepair size, peak height, peak width, peak area, unique sequence count, and combinations thereof.

According to an embodiment, the information about the sample from the analyst input module comprises one or more of a level of DNA degradation, an environmental condition, a location of the sample, and presence of an inhibitor.

According to an embodiment, the instructions for extracting data from the machine learning module comprises one or more of an allele- and locus-specific peak height ratio, an inter-locus height/intensity ratio, an intra-locus height/intensity ratio, allelic dropout, degradation, allele drop-in, inhibition, a phred score, an inter-locus baseline, an intra-locus baseline, a minimum number of contributors, a maximum number of contributors, and an estimated number of contributors.

According to an embodiment, the information about a standard data set comprises one or more metrics of an instrument utilized to obtain the parameter of the two or more nucleic acids.

According to an embodiment, the information about a standard data set comprises one or more metrics of a reaction utilized to obtain the parameter of the two or more nucleic acids.

According to an aspect, a system configured to characterize two or more nucleic acids in a sample is provided. The system includes a processor with a machine learning mixture deconvolution algorithm, where the processor is configured to: receive information comprising a parameter of the two or more nucleic acids; and determine a source and/or identity of at least one of the two or more nucleic acids.

These and other aspects of the invention will be apparent from the embodiments described below

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 4 is a schematic of input to a machine learning module of a system for DNA mixture analysis in accordance with an embodiment.

DETAILED DESCRIPTION

There is a continued need for methods and systems that perform DNA mixture interpretation using a hybrid machine learning approach in both a time-effective and cost-effective manner. Currently, a forensic scientist must perform mixture interpretation using either manual or software-supported computational methods, each requiring significant time and resources. While the forensic community has explored and implemented means such as expert systems to address the issues, these methods still have limited capabilities due in large part to the overall complexity of non-pristine DNA and lack of resources such as computational power, time and cost.

Accordingly, Applicants have provided methods and systems for an automated, intelligent system capable of performing cutting-edge DNA mixture interpretation using a hybrid machine learning approach ("MLA"). The MLA will enable rapid and automated deconvolution of DNA mixtures of multiple contributors with increased accuracy compared to current methods. The MLA will require minimal computing and financial resources and provide increasingly informative, high confidence, conclusions. The MLA permits mixture analyses using diverse data types including DNA fragment data, DNA sequence data, amplification parameters, and a wide array of instrument parameters, and post hoc data-driven parameters. This data agnostic structure allows for increased flexibility in adapting to analyses of new data types, such as next generation DNA sequence data. The design and usability focuses on requirements and limitations based on the needs of law enforcement and criminal justice communities, specifically forensic DNA scientists, policing agencies and the legal community. Accordingly, the MLA methods and systems described or otherwise envisioned herein combine an expert system with machine learning.

Figure 1:
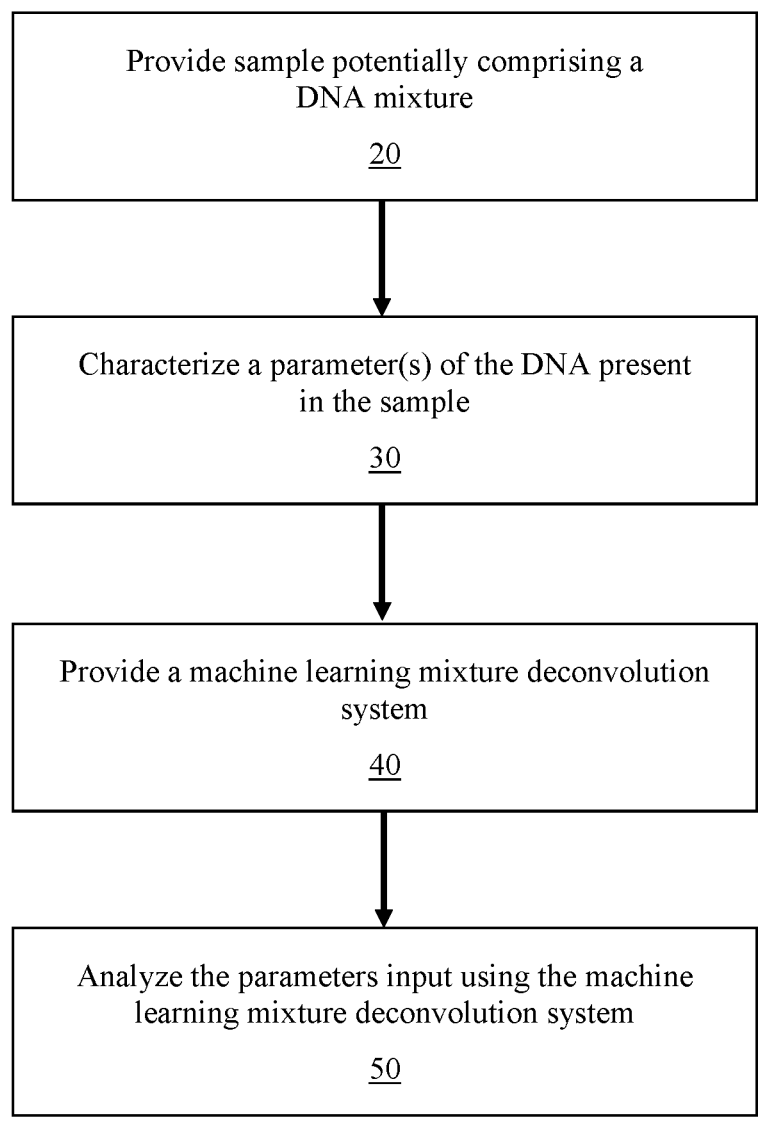
FIG. 1 is a flowchart of a method for DNA mixture analysis in accordance with an embodiment.

Referring to FIG. 1 is a flowchart of a method 10 for DNA mixture analysis in accordance with an embodiment. At step 20, a sample is provided. The sample can previously be known to include a mixture of DNA from two or more individuals, for example. Alternatively, the sample can be obtained from a location or source that is suspected of containing DNA from two or more individuals. As yet another alternative, the sample can be obtained from a location or source where it is merely possible that it could contain DNA from two or more individuals. The sample can be obtained directly in the field and then analyzed, or can be obtained at a distant location and/or time prior to analysis. Any sample that could possibly contain DNA therefore could be utilized in the analysis. According to another embodiment, the sample contains a mixture of DNA from two or more species.

At step 30, a parameter of all or part of the DNA in the sample—if DNA is present in the sample—is characterized. For example, the sample may be processed, such as by a DNA extraction and/or separation or purification step, prior to analysis. Alternatively, the sample may be analyzed without a processing step. DNA present in the sample can be characterized by, for example, capillary electrophoresis based fragment analysis, sequencing using PCR analysis with species-specific and/or species-agnostic primers, SNP analysis, one or more loci from human Y-DNA, X-DNA, and/or at DNA, or any other of a wide variety of DNA characterization methods. According to a preferred embodiment, the DNA characterization step results in one or more data files containing DNA sequence and/or loci information that can be utilized for identification of one or more sources of the DNA in the sample, either by species or individually within a species (such as a particular human being, etc.). According to advanced methods, other characteristics of the DNA may be analyzed, such as methylation patterns or other epigenetic modifications, among other characteristics.

At step 40, a machine learning mixture deconvolution system is provided. According to an embodiment, the machine learning mixture deconvolution system may be integrated into the DNA analysis component or may be separate from the DNA analysis component such that the DNA characterization information is transferred via wired or wireless communication network to the machine learning mixture deconvolution system. For example, the DNA analysis component and the machine learning mixture deconvolution system may be a single device. As another example, the DNA analysis component and the machine learning mixture deconvolution system may be present in the same building and/or laboratory, and information can be shuttled between the components in one or more directions. As yet another example, the DNA analysis component can be utilized in the field and the DNA characterization information can be transmitted via a wired or wireless network to the machine learning mixture deconvolution system.

According to an embodiment, the machine learning mixture deconvolution system learns from one or more initial data sets and then classifies mixtures from previously unseen data. Further, according to an embodiment, the machine learning is influenced from human analysts' experience-derived "rule sets." A few examples of rule sets are provided in FIG. 4, and can include a single rule set or multiple rule sets, including any of the combinations depicted in FIG. 4 and otherwise known in the art. The MLA can be developed using training data identified as directly relevant to the analysis of mixture samples, such as information about known contributors and proportions. For example, software programs exist that utilize rule sets, such as GeneMapper ID-X, OSIRIS, GeneMarker HID, TrueAllele, and STRmix. The MLA can have an associated expert system that will function in a similar, but not identical, manner. For example, the rule set can establish requirements based on expectations on the biology (i.e. genetic dosage, locus size) and methods used (i.e. amplification kits-stutter, peak balance and instrument-sensitivity, accuracy, baseline), among other factors. The rule sets could be utilized as one or more input parameters for the learning algorithm, or could be utilized as a component of the internal structure of the learning algorithm. For example, the rule set(s) could be a layer of a neuro-fuzzy network, among other possibilities. Rule sets could be layered, including in series or concurrently.

The expert system is designed to reflect the methods the human analyst would employ to analyze a sample. Further functionality of the MLA will include artifact identification (electrical spikes, raised baseline due to spectral overlap and "dye blobs") enabled through filtering by slope, area, fragment size, phred scores and/or peak maxima, among others.

The machine learning algorithm used to classify unknown contributors of a DNA mixture will have the ability to incorporate an expert system, either by embedding said system within the algorithm itself or by utilizing the system's outputs as some of the algorithm's inputs, for example. There are several machine learning algorithm types that could satisfy the requirements of the MLA, including but not limited to the following:

(1) Multi-layer perceptrons (MLP) are a form of artificial neural network having layers of nodes forming a directed graph. The initial layer of nodes, called the input layer, receives parameters used by the learning algorithm while the final layer of nodes, called the output layer, contains one node for every class that a sample could be classified. All other layers in a MLP save for the output are inner, "hidden" layers of nodes with nonlinear activation functions; these are modeled after the firing of biological neurons in the brain. An MLP using back propagation can here be considered the basic, standard algorithm for classification via supervised machine learning, and can function here, for example, as a baseline for evaluating one or more other approaches.

(2) Support vector machines (SVM) have a sound theoretical foundation originating in statistical learning theory. For a linearly separable dataset in a two-class environment, SVM finds the classification function corresponding to the maximum margin of separation between a pair of hyperplanes that divide the two classes. If no hyperplane exists that can separate the two classes entirely, a "soft margin" method finds a hyperplane that splits the examples as cleanly as possible while still maximizing the margin for cleanly split examples. The basic two-class environment can be extended to work with datasets that cannot be linearly separated and to incorporate additional classes, allowing the algorithm to classify samples into all possible combinations of genetic contributors. While SVMs are widely regarded as computationally powerful, their main drawback has historically been their corresponding computational inefficiency.

(3) Decision trees are a rule-based approach to classification and fit neatly with the project's aim to combine the computational power of machine-based learning with the expert knowledge found in more traditional forensic approaches. These traditional rule sets can be augmented using the Iterative Dichotomiser 3 algorithm (ID3) or one of its successors such as C4.5; such learning algorithms automatically generate a decision tree given an initial dataset. A C4.5-generated decision tree not only serves as a comparison to existing rule sets, but it may also suggest ways to improve those rule sets prior to their utilization by other machine learning algorithms such as MLP and SVM.

(4) Connectionist expert systems use trained neural networks instead of traditional knowledge bases and are a hybrid approach that combines a neural network with a rule-based expert system. The numerical weights associated with each edge in the neural network's directed graph correspond to the relative importance of a given rule in the rule set. Input neurons now have corresponding yes/no questions, and all inner neurons are now either rules (e.g. IF input neuron 1 and input neuron 4, THEN go to disjunction neuron 12) with associated activation values, or else disjunction nodes that automatically activate and fire to the next layer of neurons after receiving data from the network's previous layer. Such a system offers a major advantage over traditional rule-based approaches because it does not require precise matching between training data and input data.

(5) Neuro-fuzzy systems (NFS) incorporate a neural network and an initial expert-derived rule set to develop IF-THEN fuzzy rules and determine membership functions for input and output system variables. Because such systems are essentially multilayer networks, they can utilize the back propagation algorithm from MLPs to learn. An NFS, like a connectionist expert system, is a hybrid system; it attempts to combine the knowledge representation and explanatory power of a fuzzy system with learning and knowledge-discovery abilities of a neural network. In other words, the hybrid intelligent system can utilize both fuzzy systems with human-like reasoning as well as the learning ability of a neural network. Often, the FNN includes one or more fuzzy sets as well as IF-THEN fuzzy rules. According to a preferred embodiment, the FNN comprises one or more layers of neurons made up of IF-THEN rules from a fuzzified expert system of DNA mixture classification. See, e.g., FIGS. 2-4.

(6) Stacking is an ensemble learning method that combines the predictions of multiple algorithms such as those described above. All "input algorithms" are trained, and then a logistic regression model is trained to classify using the other algorithms' classifications as inputs. Stacking often produces superior classification to what any of its component algorithms offer independently. This project will evaluate multiple stacked combinations of algorithms from among the previously described algorithms.

(7) A combination of one or more of the algorithms above. The combined master algorithm could combine one or more elements of one or more of the algorithms or approaches described or otherwise envisioned herein. Alternatively, the approach may involve a series of analyses where different algorithm or algorithm groups are performed at different steps in the series.

At step 40, input is provided to the MLA. According to an embodiment, the input is the DNA characterization information. According to another embodiment, the input is obtained from one or more different sources, including but not limited to: (i) software input; (ii) analyst input; (iii) computational input; and/or (iv) validation data.

According to an embodiment, the software input fed into the software output data set can be obtained through the use of a software program that can adequately provide metrics for those parameters which are critical to the MLA analysis. Critical elements of this data set can be the quantitative assessment of the DNA types present at each DNA locus, which should not to be confused with deconvolution of DNA types. The parameters can include, but are not limited to, the total DNA amplified, the injection time and/or volume added to the reaction, the inter-run baseline, the intra-run baseline, inter-locus baseline, intra-locus baseline, allele(s)/basepair size, data points, peak height, peak width, peak area, number of peaks and/or other parameters.

According to an embodiment, the input to the MLA can encompass data that cannot be—or is not normally—captured in a laboratory analysis of the sample, or that expert systems currently available do not have the capacity to or are exceedingly complex to evaluate. These data can include the presence of low level data, DNA degradation, DNA inhibition environmental conditions during the deposition/collection/transport of the sample, location of collection, other known intelligence regarding sample collection, for example. Other data can include the presence of inhibitors, stochastic/low levels, or other information.

According to an embodiment, the MLA can include an automated method of extracting relevant data from the raw data set. These data are critical to traditional mixture interpretation and remain critical to this method. For example, computational data can include, but is not limited to, peak height balance/intensity balance/ratios, interlocus height/intensity ratios, intra locus height/intensity ratios, small and/or large locus ratios, allelic dropout, minimum number of contributors, maximum number of contributors, estimated number of contributors, weighted scenarios for the genotypes of the contributors, locus-specific threshold for allele calling and/or other parameters.

According to an embodiment, the MLA can include a laboratory-dependent static data set that can be included in every analysis. This 'known' data set can provide foundational metrics which the downstream analyses of unknown samples will be based. These data can include metrics for the instrumentation and chemistries used to obtain DNA profiles. For example, the data can include peak/intensity amplitude threshold, match interpretation threshold (stochastic threshold), sister-allele balance, artifact morphologies, stutter percent, instrument sensitivity, and/or primer amplification PCR efficiency, among other parameters.

At step 50 of the method, input is processed with the MLA to produce an output. According to an embodiment, the MLA utilizes the input from the various input components and analyzes one or more components of the DNA characterization information. Input can be analyzed via one or more parameters at one or more nodes, for example. The output can then be processed and displayed textually and/or graphically, can be transmitted to another device or location via a wired or wireless network, or can be stored for future use or analysis, for example.

Figure 2:
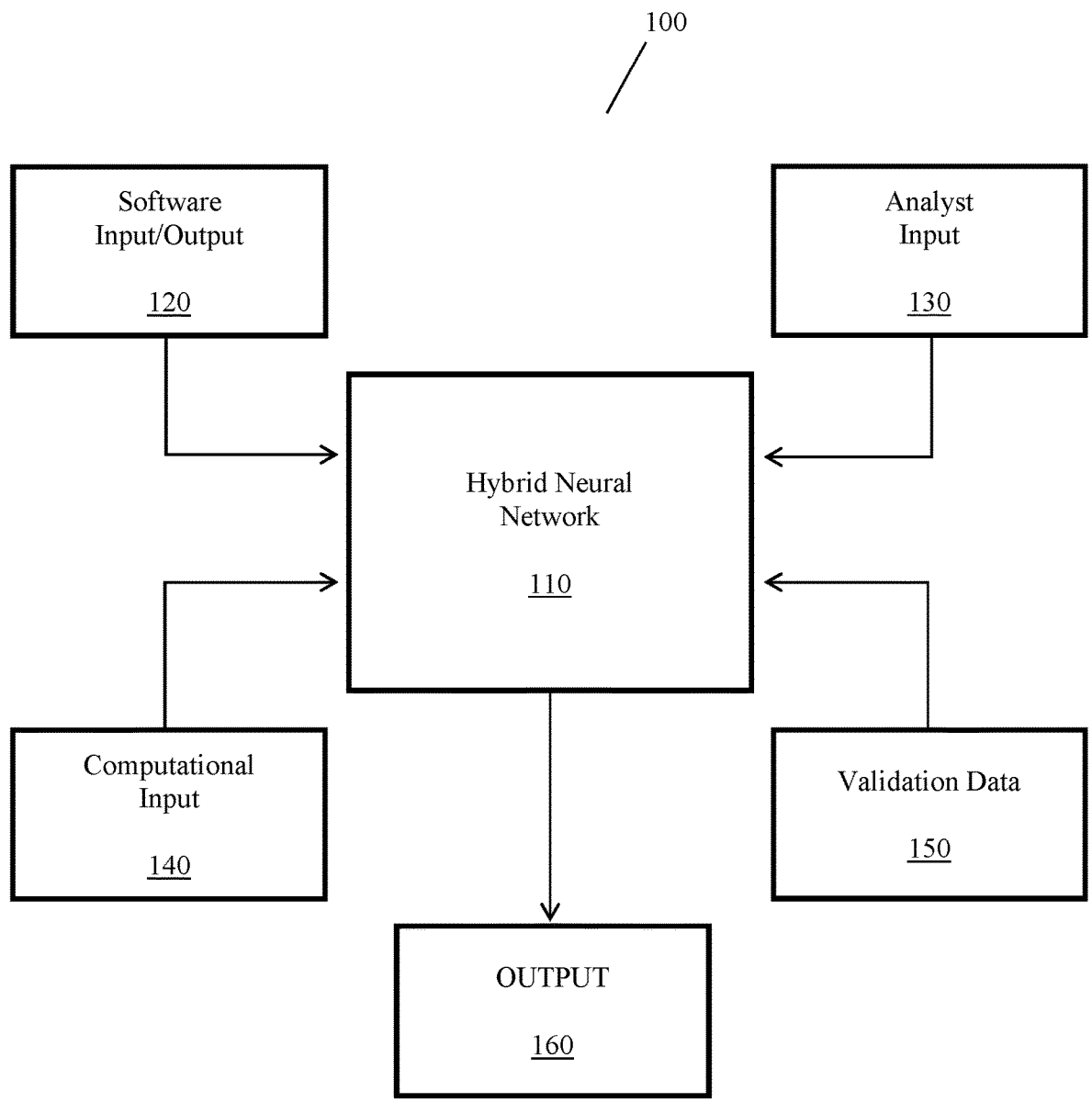
FIG. 2 is a schematic of a system for DNA mixture analysis in accordance with an embodiment.
Figure 3:
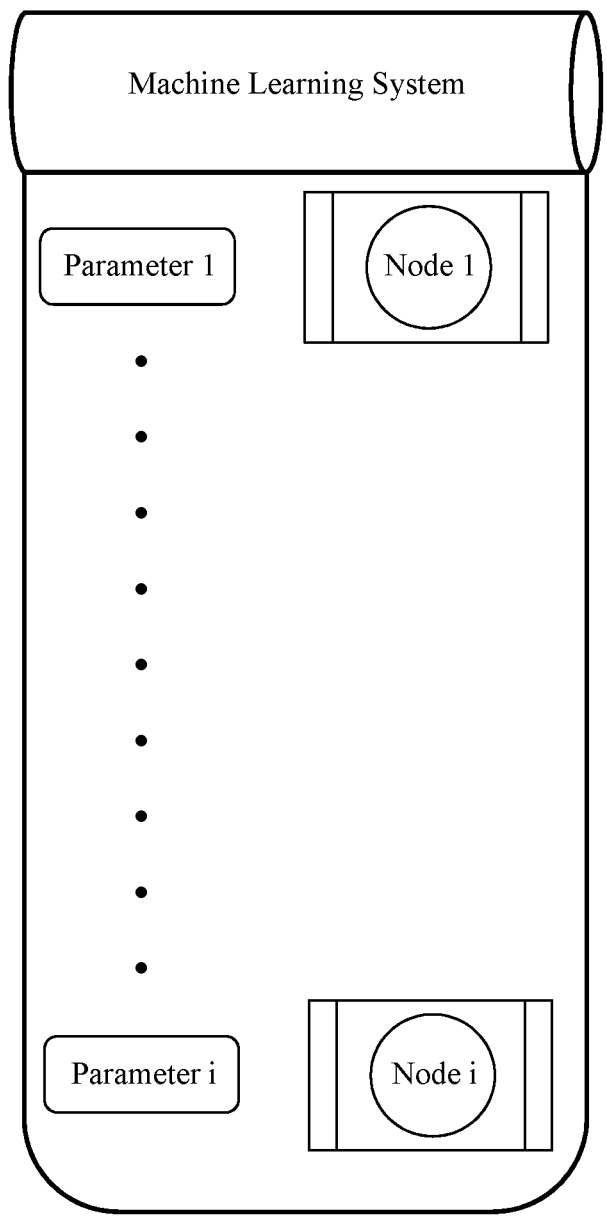
FIG. 3 is a schematic of a machine learning module of a system for DNA mixture analysis in accordance with an embodiment.

FIG. 2 is a schematic of a system 100 for DNA mixture interpretation. According to one embodiment, system 100 comprises a single unit with one or more modules, or may comprise multiple modules in more than one location that may be connected via a wired and/or wireless network connection. Alternatively, information may be moved by hand from one module to another.

As just one example of an algorithm for processing in the MLA, system 100 comprises a neuro-fuzzy neural network (FNN) module that receives input from one or more input modules, including but not limited to: (i) software input/output module 120; (ii) analyst input module 130; (iii) computational input module 140; and/or (iv) validation data module 150. According to an embodiment, the FNN comprises one or more layers of neurons made up of IF-THEN rules from a fuzzified expert system of DNA mixture classification.

Software input/output module 120 can comprise or receive or analyze, for example, input obtained through the use of a software program that can adequately provide metrics for those parameters which are critical to the FNN analysis (see, e.g., FIG. 4). Critical elements of this data set can be the quantitative assessment of the DNA types present at each DNA locus and associated instrument/methodological data. The parameters can include, but are not limited to, the total DNA amplified, DNA sequence-SNP and length variants, phred scores, the injection time and/or volume added to the reaction, the inter-run baseline, the intra-run baseline, allele(s)/basepair size, data points, peak height, peak width, peak area, unique sequence count and/or other parameters.

Analyst input module 130 can comprise or receive, for example, data that cannot be—or is not normally—captured in a laboratory analysis of the sample, or that expert systems currently available do not have the capacity to determine. These data can include the presence of low level data, DNA degradation, environmental conditions during the deposition/collection/transport of the sample, location of collection, other known intelligence regarding sample collection, for example. Other data can include the presence of inhibitors, stochastic/low levels, or other information.

Computational input module 140 can comprise instructions or systems for, or a method to, extract relevant data from the raw data set. These data are critical to traditional mixture interpretation and remain critical to this method. For example, computational data can include, but is not limited to, allele and locus specific peak height balance/intensity balance/ratios, interlocus height/intensity ratios, intra locus height/intensity ratios, allele size small and/or large locus ratios, allelic dropout, degradation, allele drop-in, inhibition, Phred scores, inter-locus baseline, intra-locus baseline, locus and allele specific stutter percentages, minimum, maximum and estimated number of contributors, and/or other parameters.

Validation data module 150 can, for example, be a laboratory-dependent static data set that can be included in every analysis. This 'known' data set can provide foundational metrics which the downstream analyses of unknown samples will be based. These data can include metrics for the instrumentation and chemistries used to obtain DNA profiles. For example, the data can include peak/intensity amplitude threshold, match interpretation threshold (stochastic threshold), heterozygote balance, artifact morphologies, locus specific stutter percent, instrument sensitivity, and/or primer PCR efficiency, among other parameters.

According to an embodiment, input is processed by FNN 110 to produce an output 160. According to an embodiment, the FNN utilizes the input from the various input components and analyzes one or more components of the DNA characterization information. Input can be analyzed via one or more parameters at one or more nodes, for example. The output can then be processed and displayed textually and/or graphically, can be transmitted to another device or location via a wired or wireless network, or can be stored for future use or analysis, for example.

One or more of the software input/output module 120, analyst input module 130, computational input module 140, validation data module 150, and the hybrid neural network can be implemented by hardware and/or software, including but not limited to a processor, computer system, database, computer program, and others. The hardware and/or software can be implemented in different systems or can be implemented in a single system.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

A "module" or "component" as may be used herein, can include, among other things, the identification of specific functionality represented by specific computer software code of a software program. A software program may contain code representing one or more modules, and the code representing a particular module can be represented by consecutive or non-consecutive lines of code.

As will be appreciated by one skilled in the art, aspects of the present invention may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowcharts/block diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A computer system for determining a genotype of each contributor to a DNA sample containing DNA of a plurality of unknown contributors, the computer system comprising:
   a storage medium containing amplified DNA sequence data from the amplified DNA sample containing the plurality of unknown contributors, wherein the amplified DNA sequence data is characterized according to a set of computational data parameters comprising, for each locus in the first sample of the amplified DNA sequence data, a peak area, a peak height, an allelic dropout, an allelic drop-in, an estimated number of contributors, and for the first sample of the amplified DNA sequence data, a peak count, a total amount of DNA amplified, and a sequence count;

a processor programmed with a machine learning algorithm, wherein the processor is programmed to train the machine learning algorithm using at least one set of known amplified DNA sequence data, from a sample having DNA of a plurality of known contributors and a set of known computational data parameters of that sequence data to generate a trained machine learning algorithm based on the set of computational data parameters of the at least one known sample, wherein the machine learning algorithm is selected from the group consisting of a neural network, a multi-layer perceptron, a support vector machine, a decision tree, a neuro-fuzzy system, and combinations thereof; and wherein the processor is further programmed to apply the trained machine learning algorithm to deconvolute the characterized sequence data of the amplified DNA containing the DNA of a plurality of unknown contributors to determine the number of unknown contributors to that DNA sample and to output a genotype for each of the unknown contributors to the amplified DNA of the DNA sample containing the DNA of a plurality of unknown contributors.

2. The system of claim 1, wherein the machine learning algorithm comprises the neural network.

3. The system of claim 1, wherein the machine learning algorithm comprises the multi-layer perceptron.

4. The system of claim 1, wherein the machine learning algorithm comprises the support vector machine.

5. The system of claim 1, wherein the machine learning algorithm comprises the decision tree.

6. The system of claim 1, wherein the machine learning algorithm comprises a combination of the decision tree and the support vector machine.

* * * * *